(12) United States Patent
Murphy et al.

(10) Patent No.: US 7,093,491 B2
(45) Date of Patent: Aug. 22, 2006

(54) APPARATUS AND METHODS FOR AUTOMATED TURBINE COMPONENT INSPECTIONS

(75) Inventors: Thomas Francis Murphy, Scotia, NY (US); Robert M. Roney, Jr., Schoharie, NY (US)

(73) Assignee: General Electric Company, Schenectady, NY (US)

( * ) Notice: Subject to any disclaimer, the term of this patent is extended or adjusted under 35 U.S.C. 154(b) by 157 days.

(21) Appl. No.: 10/821,336

(22) Filed: Apr. 9, 2004

(65) Prior Publication Data
US 2005/0223809 A1    Oct. 13, 2005

(51) Int. Cl.
*G01N 29/265* (2006.01)

(52) U.S. Cl. .......................................... 73/620; 73/633
(58) Field of Classification Search .................. 73/618, 73/619, 620, 621, 624, 625, 633, 634
See application file for complete search history.

(56) References Cited

U.S. PATENT DOCUMENTS

| | | | |
|---|---|---|---|
| 3,678,736 A * | 7/1972 | May | 73/634 |
| 4,290,309 A | 9/1981 | Charlebois et al. | |
| 5,606,262 A | 2/1997 | Montalbano et al. | |
| 5,710,378 A * | 1/1998 | Dykes et al. | 73/601 |
| 6,065,344 A | 5/2000 | Nolan et al. | |
| 6,082,198 A | 7/2000 | Sabourin et al. | |
| 6,198,280 B1 | 3/2001 | Hensley | |
| 6,408,695 B1 | 6/2002 | Bewlay | |
| 6,424,922 B1 | 7/2002 | Bray | |
| 6,477,473 B1 | 11/2002 | Bray | |
| 6,563,307 B1 | 5/2003 | Trantow | |
| 6,596,099 B1 | 7/2003 | Bewley et al. | |
| 6,795,809 B1 * | 9/2004 | O'Brien et al. | 705/16 |

FOREIGN PATENT DOCUMENTS

| | | |
|---|---|---|
| GB | 1554721 A | 10/1979 |
| GB | 2195022 A | 8/1986 |

OTHER PUBLICATIONS

International Search Report, dated Aug. 12, 2005, Application No. GB0505390.5, 3 pgs.

* cited by examiner

*Primary Examiner*—Hezron Williams
*Assistant Examiner*—Rose M. Miller
(74) *Attorney, Agent, or Firm*—Armstrong Teasdale LLP

(57) ABSTRACT

An inspection system, in an exemplary embodiment, includes at least two base members spaced apart from each other, a support arm mounted to each base member, a linear track extending between and supported by the support arms, and a transport member coupled to the linear track. The transport member is movable along the linear track. The system further includes a transducer support arm pivotably coupled to the transport member, and a transducer assembly coupled to the transducer support arm.

23 Claims, 4 Drawing Sheets

APPARATUS AND METHODS FOR AUTOMATED TURBINE COMPONENT INSPECTIONS

BACKGROUND OF THE INVENTION

This invention relates generally to automated ultrasound and eddy current inspection systems, and more particularly to automated inspection systems for turbine and generator rotors and wheels.

Manual inspections of rotor forgings and related components have been performed for many years to inspect for flaws in the forgings. Because of the difficulties and inaccuracies associated with manual ultrasonic and eddy current tests, two separate manual tests are typically performed on rotors to increase the reliability of the inspection.

Manual ultrasonic inspection of rotor forgings include a radial test from the periphery of the rotor forging directed toward the center of the forging. An inspector watches the ultrasonic test instrument looking for reflectors. The operator then peaks the reflector and records its location and amplitude. An inattentive inspector an easily miss indications due to momentary distractions, an incorrect setup, as well as monotony and tedium.

In some cases a semi-automated system has been used to inspect rotor forgings. The system captured the inspection waveforms and permitted an inspector to identify possible flaw indications located within the rotor. The inspector then returned to the identified areas and performed a manual ultrasonic inspection to confirm the flaw indication as well as determine the peak amplitude of the indication. The peak amplitude is used to determine the size of embedded flaw. The semi-automated system requires a manual exam to verify defect amplitude and location.

BRIEF DESCRIPTION OF THE INVENTION

In one aspect, an inspection system is provided. The inspection system includes at least two base members spaced apart from each other, a support arm mounted to each base member, a linear track extending between and supported by the support arms, and a transport member coupled to the linear track. The transport member is movable along the linear track. The inspection system further includes a transducer support arm pivotably coupled to the transport member, and a transducer assembly coupled to the transducer support arm.

In another aspect, an inspection system for inspecting metal articles is provided. The inspection system includes a base member, a support arm mounted to the base member, a linear track mounted to the support arm, and a transport member coupled to the linear track. The transport member is movable along the linear track. The inspection system further includes a transducer support arm pivotably coupled to the transport member, and a transducer assembly coupled to the transducer support arm.

In another aspect, a method of inspecting a metal article is provided. The method includes positioning an inspection apparatus adjacent the metal article, and inspecting the metal article utilizing the inspection apparatus. The inspection apparatus includes at least two base members, the base members spaced apart from each other, a support arm mounted to each base member, a linear track extending between and supported by the support arms, the track having a first side and a second side, a transport member coupled to the linear track, the transport member movable along the linear track, a transducer support arm pivotably coupled to the transport member, and a transducer assembly coupled to the transducer support arm.

DETAILED DESCRIPTION OF THE INVENTION

An automated inspection system for ultrasonic and/or eddy current inspections of metal articles, for example, turbine forgings is described below in detail. The system is portable and can be moved to various locations for rotor, wheels, or disc forging inspections. The inspection system is capable of passively monitoring translational and rotary motion, and can be used on disc shapes, hollow cylinders, solid cylinders, and/or plate shapes. The passive positional monitoring permits the use of existing component manipulation devices such as lathes, boring mills, and X-Y motion systems for probe motion relative to the part tested. For cylindrical or disc shaped forgings, existing component manipulation devices are used to move the part relative to the probes so that the probe path over the surface of the part is in a helical or spiral pattern depending upon the shape of the forging. Also, the passive monitoring of the motion control source permits the inspection system to be used on various machinery without a specific configuration for any particular machining device. The system is described below in relation to rotor forgings for steam turbines, however, the system can also be used in relation to forgings for gas turbine, generators, and other rotational machines.

Figure 1:
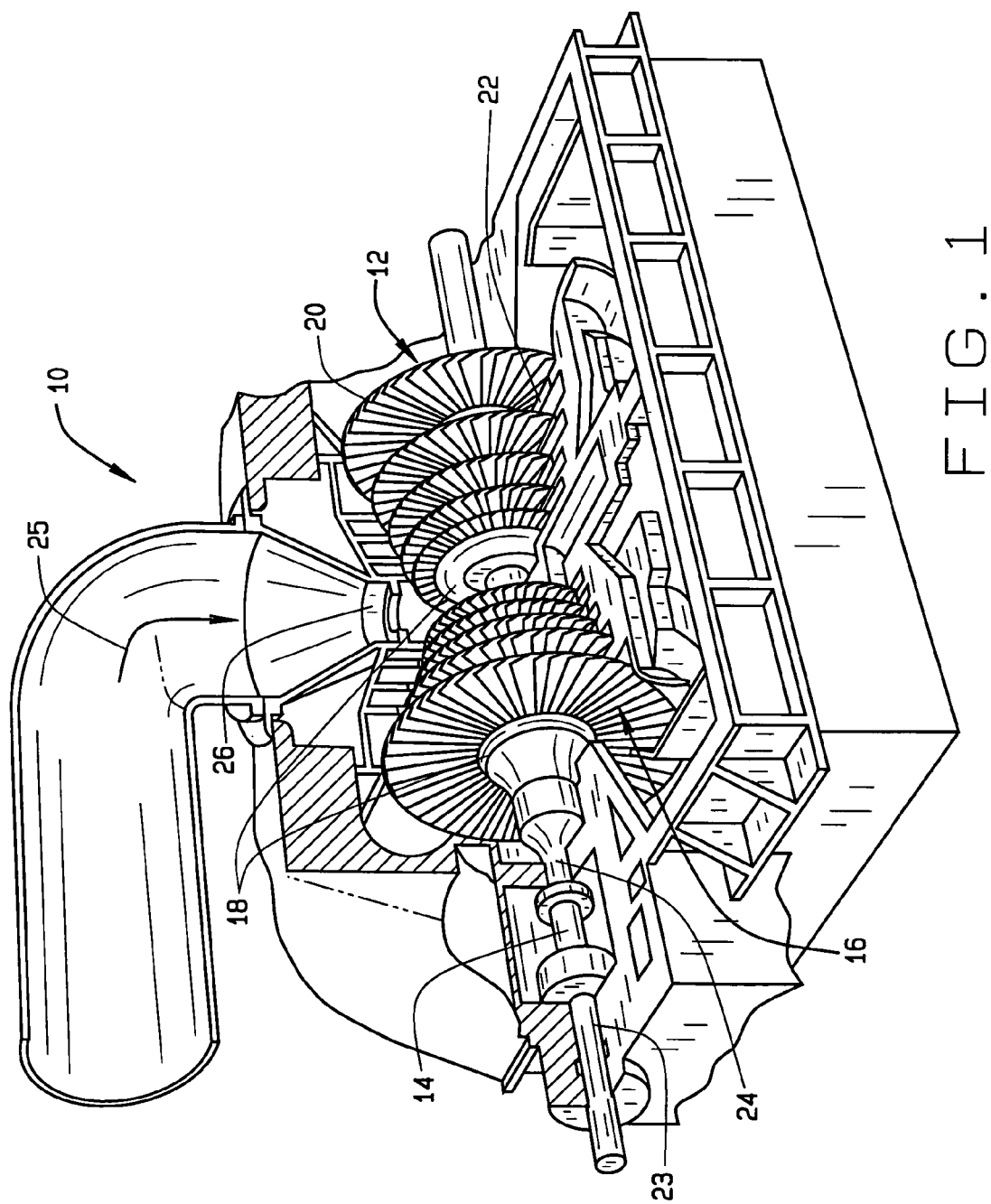
FIG. 1 is a perspective partial cut away view of an exemplary steam turbine.

Referring to the drawings, FIG. 1 is a perspective partial cut away view of an exemplary steam turbine 10 including a rotor 12 that includes a shaft 14 and a plurality of turbine stages 16. Turbine rotor 12 includes a plurality of axially spaced rotor wheels 18. In one exemplary embodiment, rotor wheels 18 are formed from forgings that are machined to the desired configuration. A plurality of buckets 20 are mechanically coupled to each rotor wheel 18. More specifically, buckets 20 are arranged in rows that extend circumferentially around each rotor wheel 18. A plurality of stationary nozzles 22 extend circumferentially around shaft 14 and are axially positioned between adjacent rows of buckets 20. Nozzles 22 cooperate with buckets 20 to form each turbine stage 16 and to define a portion of a steam flow path through turbine 10. Shaft 14 is supported and guided in rotation by a plurality of bearings 23 and 24.

In operation, steam 25 enters an inlet 26 of turbine 10 and is channeled through nozzles 22. Nozzles 22 direct steam 25 downstream against buckets 20. Steam 25 passes through the remaining stages 16 imparting a force on buckets 20 which causes rotor 12 to rotate. At least one end of turbine 10 may extend axially away from rotor 12 and may be attached to a load or machinery (not shown), such as, but not limited to, a generator, and/or another turbine. Accordingly, a large steam turbine unit may actually include several turbines that are all co-axially coupled to the same shaft 14. Such a unit may, for example, include a high-pressure (HP) turbine coupled to an intermediate-pressure (IP) turbine, which is coupled to a low-pressure (LP) turbine. In one embodiment, steam turbine 10 is commercially available from General Electric Power Systems, Schenectady, N.Y.

Figure 2:
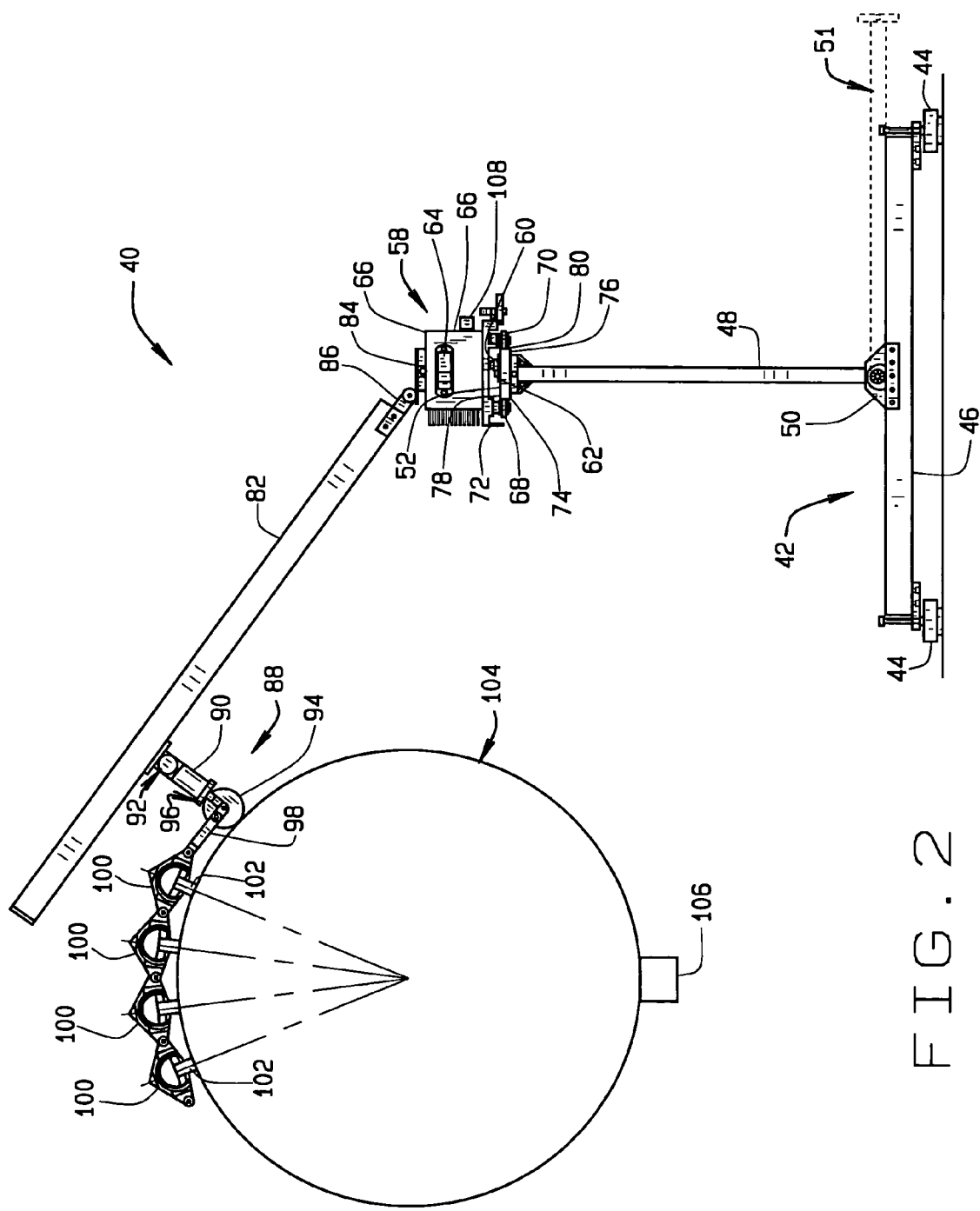
FIG. 2 is a front view of an inspection system in accordance with an exemplary embodiment of the present invention.
Figure 3:
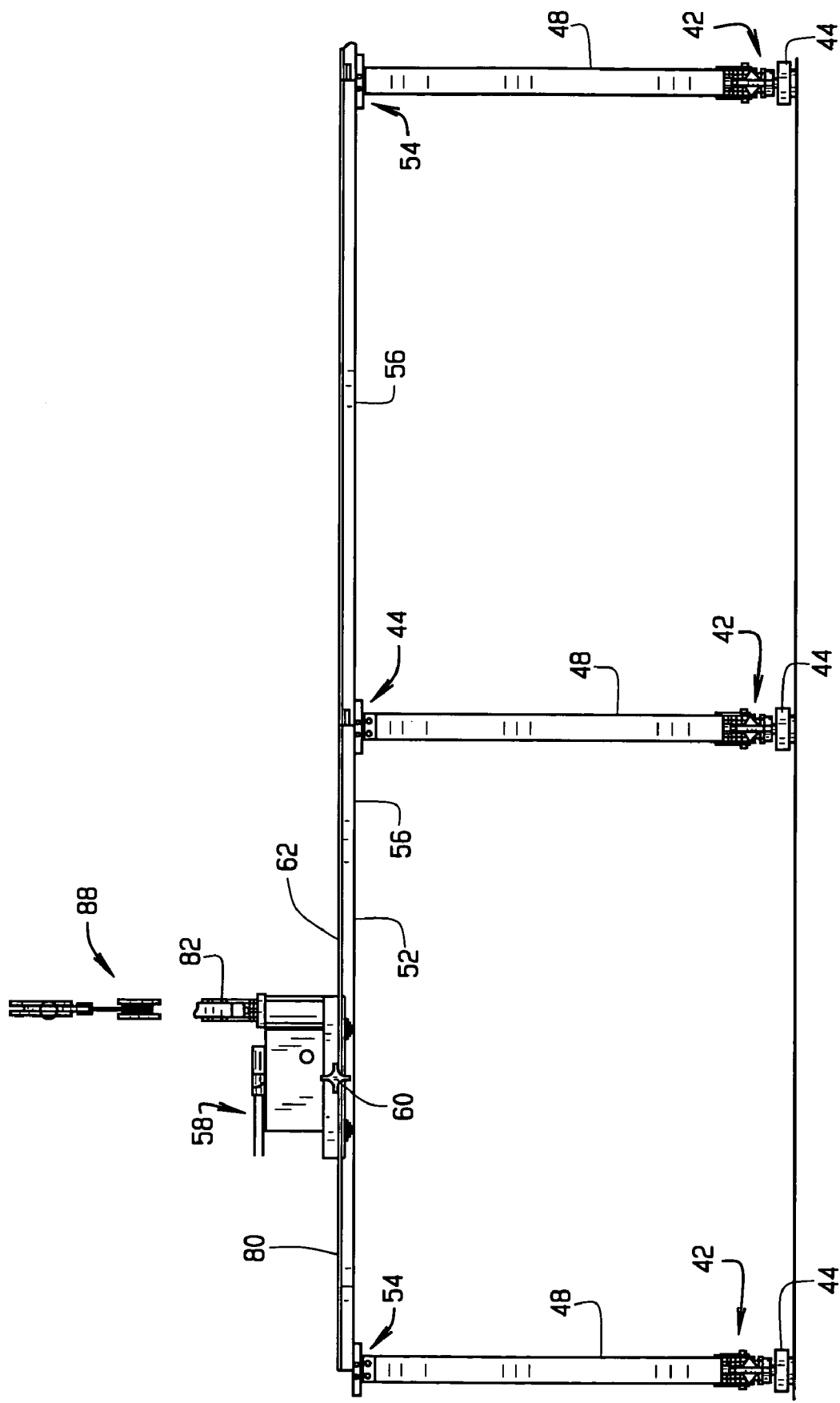
FIG. 3 is a side view of the inspection system shown in FIG. 2.

FIG. 2 is a front view of an exemplary embodiment of an automated inspection system 40, and FIG. 3 is a side view of inspection system 40. Referring to FIGS. 2 and 3, inspection system 40 includes base members 42 spaced apart from each other. Each base member 42 includes adjustable support feet 44 and a support beam 46 extending between and coupled to support feet 44. A support arm 48 is mounted to support beam 46 by a bracket 50 that permits support arm 48 to be pivoted to a stored position 51 for shipping which is represented by the dotted lines in FIG. 2. A linear track 52 extends between support arms 48 and is mounted to an end 54 of support arms 48. Linear track 52 is formed by linear track sections 56 positioned end to end.

A transport member 58 is coupled to linear track 52 and is movable along track 52. Transport member 58 includes a spur gear 60 sized to mate with a rack 62 attached to track 52. A drive motor 64 is located inside a transport member housing 66 and is operationally coupled to spur gear 60. Guide rollers 68 and 70 extend from a base portion 72 of transport member 58. Guide rollers 68 are positioned to engage a first side 74 of track 52 and guide rollers 70 are positioned to engage a second side 76 of track 52. Guide rollers 68 and 70 are configured to ride in grooves 78 and 80 in first and second sides 74 and 76 of track 52 respectively. Roller guides 68 and 70 permit transport member 58 to move along track 50 as spur gear 60 turns to drive transport member 58. In alternate embodiments, transport member 58 includes other means of motion along track 50, for example a drive chain, a drive cable, and one or more drive wheels.

A transducer support arm 82 is coupled to a top portion 84 of transport member 58 by a pivot bracket 86. A transducer assembly 88 is coupled to transducer support arm 82. Transducer assembly 88 includes an attachment member 90 coupled at a first end 92 to transducer support arm 82. A support wheel 94 is coupled to a second end 96 of attachment member 90. A link arm 98 is also attached to second end 96 of attachment member 90. Transducer holders 100 are coupled to each other and to link arm 98. An ultrasonic transducer probe 102 is mounted in each transducer holder 100. In another embodiment, an eddy current probe is mounted in each holder 100 Transducer holders 100 are positioned end to end and are pivotably coupled to each other to permit inspection of various shaped and sized forgings.

To inspect a rotor forging 104, inspection system 40 is positioned adjacent forging 104. Specifically, base members 42 are positioned on the floor 106 and leveled by adjusting support feet 44. Linear track 52 is mounted on support arms 48 attached to each base 42. Transport member 58 is positioned on track 52 with spur gear 60 mating with rack 60 and guide rollers 68 and 70 engaging grooves 78 and 80 in track 52. Linear track 52 is orientated in the desired axis of motion for ultrasonic probes 102. Transport member 58 is moved along track 52 and into position adjacent forging 104 so that transducer support arm 88 is positioned adjacent forging 104 with ultrasonic transducer probes 102 and wheel 94 contacting the surface of forging 104. Rotor forging 104 is rotated using an existing forging manipulation device (not shown) while probes 102 scan forging 104. Scan data is collected by a data acquisition system (not shown). When a first position sensor 106 determines that a complete rotation of forging 104 has been examined, transport member 58 is moved along track 52 to reposition ultrasonic transducer probes 102 so as to scan an adjacent portion of forging 104. A second position sensor 108 monitors the linear movement of transport member 58 along linear track 52. These steps are repeated until the entire volume of forging 104 has been inspected. In an alternate embodiment, eddy current probes are used to inspect forging 104 rather than ultrasonic transducer probes.

Figure 4:
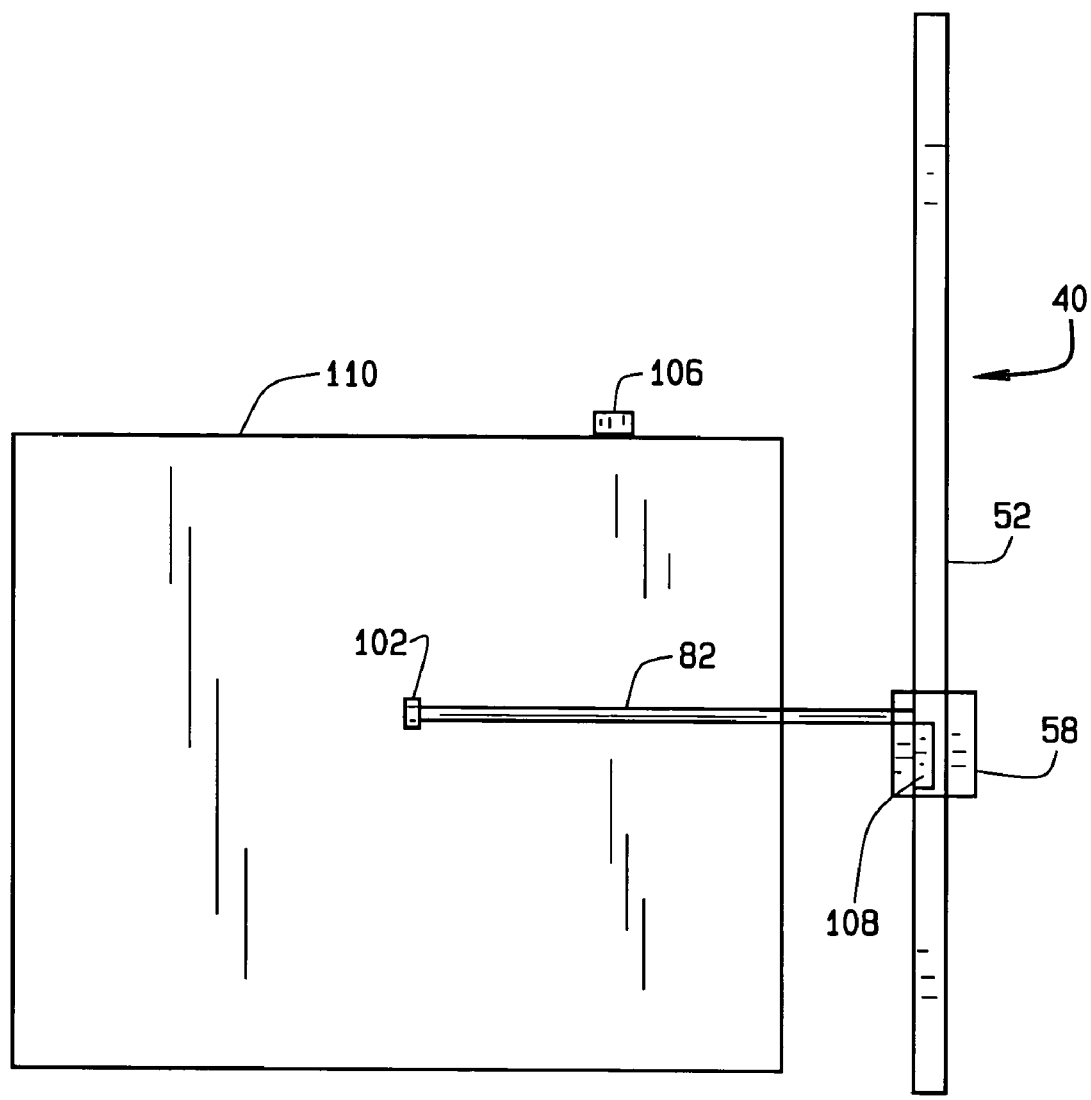
FIG. 4 is a top schematic illustration of the inspection system shown in FIG. 2 and a plate shaped forging.

FIG. 4 is a top schematic illustration of inspection system 40 inspecting a plate shaped forging 110. To inspect plate shaped forging 110, inspection system 40 is positioned adjacent forging 110. Linear track 52 is orientated in the desired axis of motion for ultrasonic probes 102. Transport member 58 is moved along track 52 and into position adjacent forging 104 so that transducer support arm 88 is positioned adjacent forging 110 with ultrasonic transducer probes 102 contacting the surface of forging 110. Forging 110 is moved along the X-axis using an-existing forging manipulation device (not shown) while probes 102 scan forging 110. Scan data is collected by a data acquisition system (not shown). When first position sensor 106 determines that probes 102 have traversed forging 110, transport member 58 is moved along track 52 in the Y-axis to reposition ultrasonic transducer probes 102 so as to scan an adjacent portion of forging 110. Second position sensor 108 monitors the linear movement of transport member 58 along linear track 52. These steps are repeated until the entire volume of forging 110 has been inspected. In an alternate embodiment, eddy current probes are used to inspect forging 110 rather than ultrasonic transducer probes.

Figure 5:
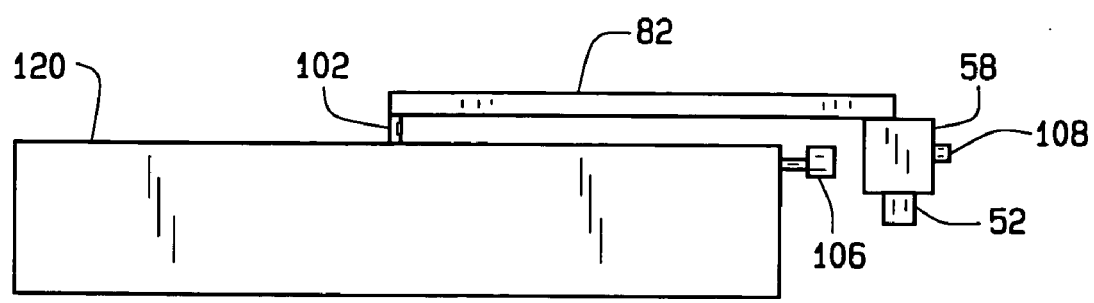
FIG. 5 is a side schematic illustration of the inspection system shown in FIG. 2 and a disc shaped forging.

FIG. 5 is a side schematic illustration of inspection system 40 inspecting a disc shaped forging 120. To inspect disc shaped forging 120, inspection system 40 is positioned adjacent forging 120. Linear track 52 is orientated in the desired axis of motion for ultrasonic probes 102. Transport member 58 is moved along track 52 and into position adjacent forging 104 so that transducer support arm 88 is positioned adjacent forging 120 with ultrasonic transducer probes 102 contacting the surface of forging 120. Forging 120 is rotated using an existing forging manipulation device (not shown) while probes 102 scan forging 120. Scan data is collected by a data acquisition system (not shown). When first position sensor 106 determines that a complete rotation of forging 120 has been examined, transport member 58 is moved along track 52 to reposition ultrasonic transducer probes 102 so as to scan an adjacent portion of forging 120 in a spiral shaped pattern. A second position sensor 108 monitors the linear movement of transport member 58 along linear track 52. In an alternate embodiment, eddy current probes are used to inspect forging 120 rather than ultrasonic transducer probes.

In the exemplary embodiment illustrated in FIGS. 2 and 3, linear track 50 is positioned in a substantially horizontal orientation, i.e., substantially parallel to the floor. However, in other embodiments, linear track 50 can be positioned in other orientations, for example, in an inclined orientation or in a vertical orientation.

While the invention has been described in terms of various specific embodiments, those skilled in the art will recognize that the invention can be practiced with modification within the spirit and scope of the claims.

What is claimed is:

1. An inspection system comprising:
   at least two base members, said base members spaced apart from each other;

a support arm mounted to each said base member;
a linear track extending between and supported by said support arms, said track comprising a first side and a second side;
a transport member coupled to said linear track, said transport member movable along said linear track;
a transducer support arm pivotably coupled to said transport member; and
a transducer assembly coupled to said transducer support arm, wherein said transducer assembly comprises an attachment member coupled at a first end to said transducer support arm and a support wheel coupled to a second end of said attachment member.

2. An inspection system in accordance with claim 1 wherein said transport member comprises a spur gear and said linear track comprises a rack, said spur gear configured to operationally couple to said rack to move said transport member along said track.

3. An inspection system in accordance with claim 2 wherein said transport member comprises a plurality of guide rollers positioned to engage said first and second sides of said track.

4. An inspection system in accordance with claim 1 wherein said linear track comprises a plurality of track sections.

5. An inspection system in accordance with claim 1 wherein said transducer assembly comprises:
a link arm coupled to said second end of said attachment member;
at least one transducer holder coupled to said link arm; and
at least one of an ultrasonic transducer and an eddy current transducer mounted in each said transducer holder.

6. An inspection system in accordance with claim 5 wherein said transducer assembly comprises at least two transducer holders, said transducer holders arranged linearly end to end and pivotably attached to each other.

7. An inspection system in accordance with claim 1 further comprising a first position encoder positioned adjacent said transport member and a second position encoder positioned adjacent an article to be inspected, said first position encoder configured to determine a first axis positioning of said transport member and said second position encoder configured to determine a radial or second axis positioning of the article.

8. An inspection system for inspecting metal articles, the inspection system comprising:
a base member;
a support arm mounted to said base member;
an elongate linear track mounted to said support arm, said track comprising a first side and a second side, wherein a length of said track extends generally perpendicularly to said support arm;
a transport member coupled to said linear track, said transport member movable along said linear track;
a transducer support arm pivotably coupled to said transport member; and a transducer assembly coupled to said transducer support arm.

9. An inspection system in accordance with claim 8 comprising at least two base members.

10. An inspection system in accordance with claim 9 comprising at least two support arms, each said support arm mounted on a corresponding base member.

11. An inspection system in accordance with claim 8 wherein said transport member comprises a spur gear and said linear track comprises a rack, said spur gear configured to operationally couple to said rack to move said transport member along said track.

12. An inspection system in accordance with claim 11 wherein said transport member comprises a plurality of guide rollers positioned to engage said first and second sides of said track.

13. An inspection system in accordance with claim 8 wherein said linear track comprises a plurality of track sections.

14. An inspection system in accordance with claim 8 wherein said transducer assembly comprises:
an attachment member coupled at a first end to said transducer support arm;
a support wheel coupled to a second end of said attachment member;
a link arm coupled to said second end of said attachment member;
at least one transducer holder coupled to said link arm; and
at least one of an ultrasonic transducer and an eddy current transducer mounted in each said transducer holder.

15. An inspection system in accordance with claim 14 wherein said transducer assembly comprises at least two transducer holders, said transducer holders arranged linearly end to end and pivotably attached to each other.

16. An inspection system in accordance with claim 8 further comprising a first position encoder positioned adjacent said transport member and a second position encoder positioned adjacent an article to be inspected, said first position encoder configured to determine a first axis positioning of said transport member and said second position encoder configured to determine a radial or second axis positioning of the article.

17. A method of inspecting a metal article, said method comprising:
positioning an inspection apparatus adjacent the metal article; and
inspecting the metal article utilizing the ultrasonic inspection apparatus;
the inspection apparatus comprising:
at least two base members, the base members spaced apart from each other;
a support arm pivotally mounted to each base member such that the support arms are each be pivotable relative to the corresponding base member;
a linear track extending between and supported by the support arms, the track comprising a first side and a second side;
a transport member coupled to the linear track, the transport member movable along the linear track;
a transducer support arm pivotably coupled to the transport member; and
a transducer assembly coupled to the transducer support arm.

18. A method in accordance with claim 17 wherein the transport member comprises a plurality of guide rollers and a spur gear, the linear track comprises a rack, the spur gear configured to operationally couple to the rack to move the transport member along the linear track, said inspecting the metal article comprising repositioning the transducer assembly by moving the transport member along the linear track.

19. A method in accordance with claim 17 wherein the transducer assembly comprises:
an attachment member coupled at a first end to the transducer support arm;

a support wheel coupled to a second end of the attachment member;

a link arm coupled to the second end of the attachment member;

at least one transducer holder coupled to the link arm; and at least one of an ultrasonic transducer and an eddy current transducer mounted in each transducer holder.

20. A method in accordance with claim 19 wherein the transducer assembly comprises at least two transducer holders, the transducer holders arranged linearly end to end and pivotably attached to each other.

21. A method in accordance with claim 19 wherein the ultrasonic inspection system further comprises a first position encoder positioned adjacent the transport member and a second position encoder positioned adjacent the metal article, the first position encoder configured to determine a first axis positioning of the transport member and the second position encoder configured to determine a radial or second axis positioning of the metal article, said inspecting the metal article further comprising:

moving the metal article in relation to the transducer assembly; and determining the position of the metal article in relation to each transducer with the first and second position encoders.

22. A method in accordance with claim 17 wherein the metal article is a forging.

23. A method in accordance with claim 22 wherein the forging is a component of a gas turbine, a steam turbine, or a generator.

* * * * *